(12) United States Patent
Schramm et al.

(10) Patent No.: US 8,580,771 B2
(45) Date of Patent: Nov. 12, 2013

(54) DOSAGE FORM FOR HORMONAL CONTRACEPTION

(75) Inventors: Georg Schramm, Stolberg (DE); Eric-Paul Paques, Aachen (DE)

(73) Assignee: Richter Gedeon Nyrt., Budapest (HU)

( * ) Notice: Subject to any disclaimer, the term of this patent is extended or adjusted under 35 U.S.C. 154(b) by 2098 days.

(21) Appl. No.: 11/244,974

(22) Filed: Oct. 6, 2005

(65) Prior Publication Data

US 2006/0089338 A1   Apr. 27, 2006

Related U.S. Application Data

(63) Continuation-in-part of application No. 11/009,817, filed on Dec. 10, 2004, now abandoned, and a continuation-in-part of application No. 11/009,938, filed on Dec. 10, 2004.

(30) Foreign Application Priority Data

May 28, 2004  (DE) .......................... 10 2004 026 670
May 28, 2004  (DE) .......................... 10 2004 026 671

(51) Int. Cl.
*A61K 31/56* (2006.01)
*A61K 31/495* (2006.01)

(52) U.S. Cl.
USPC ............................ 514/171; 514/169; 514/249

(58) Field of Classification Search
None
See application file for complete search history.

(56) References Cited

U.S. PATENT DOCUMENTS

| | | | |
|---|---|---|---|
| 6,190,693 B1 * | 2/2001 | Kafrissen et al. ............. | 424/451 |
| 6,265,393 B1 | 7/2001 | Heinrichs ...................... | 514/178 |
| 6,312,722 B1 * | 11/2001 | Schmidt-Gollwitzer et al. ............................... | 424/464 |
| 6,500,814 B1 * | 12/2002 | Hesch ........................... | 514/170 |
| 6,511,970 B1 | 1/2003 | Rodriguez | |
| 2002/0010167 A1 | 1/2002 | Grubb ........................... | 514/182 |
| 2002/0061875 A1 | 5/2002 | Gast | |
| 2004/0063721 A1 | 4/2004 | Deecher | |

FOREIGN PATENT DOCUMENTS

| | | |
|---|---|---|
| DE | 4104385 C1 | 2/1991 |
| DE | 4224534 A1 | 7/1992 |
| DE | 4308406 C1 | 3/1993 |
| DE | 4321957 C2 | 9/1995 |
| DE | 3486422 T2 | 6/1997 |
| DE | 698 04 918 T2 | 6/1998 |
| DE | 19705229 C2 | 4/1999 |
| DE | 19739916 C2 | 9/2001 |
| DE | 69804918 T2 | 11/2002 |
| DE | 60101276 T2 | 4/2004 |
| EP | 0253607 | 1/1988 |
| EP | 0253607 A1 | 1/1988 |
| EP | 0398460 A2 | 5/1990 |
| EP | 0398460 A3 | 5/1990 |
| EP | 0398460 B1 | 5/1990 |
| EP | 0398460 A2 | 11/1990 |
| EP | 0398460 A3 | 11/1990 |
| WO | WO 86/01402 | 3/1986 |
| WO | WO 99/53910 | 10/1999 |
| WO | WO 00/38691 | 7/2000 |
| WO | WO 00/44385 | 8/2000 |
| WO | 02/22110 A2 | 3/2002 |
| WO | WO 02/094276 A1 | 11/2002 |
| WO | WO 2004/098517 A2 | 11/2004 |

OTHER PUBLICATIONS

"Effect of 21-day and 24-day oral contraceptive regimens containing gestodene (60 μg) and ethinyl estradiol (15 μg) on ovarian activity", Helen Sullivan et al., Fertility and Sterility, vol. 72, No. 1, Jul. 1999, 115-120.

"The safety and contraceptive efficacy of a 24-day low-dose oral contraceptive regimen containing gestodene 60 μg and ethinylestradiol 15 μg", Gestodene Study Group 322, The European Journal of Contraception and Reproductive Health Care, 1999, (Suppl. 2): 9-15.

"Folic Acid Awareness and Use Among Women With A History of a Neural Tube Defect Pregnancy", Canfield et al., MMWR Recomm Rep. Sep. 13, 2002; 51(RR-13):16-9.

"Effect of 21-day and 24-day Oral Contraceptive Regimens Containing Gestodene (60μg) and Ethinyl Estradiol (15μg) on Ovarian Activity", Helen Sullivan et al., Fertility and Sterility, vol. 72, No. 1, Jul. 1999, 115-120.

"Properties of Reactively Evaporated Gallium Oxide Thin Films", Mar. 1979, XP-000905106, pp. 13-17.

Acne Resolution Rates: Results of a Single-Blind, Randomized, Controlled, Parallel Phase III Trial with EE/CMA (Belara®) and EE/LNG (Microgynon®), I. Worret, et al., Pharmacology and Treatment, Dermatology 2001; 203:38-44.

"Chlormadinone acetate versus micronized progesterone in the sequential combined hormone replacement therapy of the menopause", C. Pelissier, et al., XP-002349010, Maturitas 40 (2001) 85-94.

Non Final Office Action issued on Mar. 12, 2009 by Examiner for corresponding pending U.S. Appl. No. 11/009,361.

(Continued)

*Primary Examiner* — Sreeni Padmanabhan
*Assistant Examiner* — Jody Karol
(74) *Attorney, Agent, or Firm* — Jason D. Voight

(57) ABSTRACT

A dosage form for hormonal contraception containing a given number of hormone-containing daily units and a given number of hormone-free daily units for daily, oral administration, where the hormone-containing daily units each contain at most the minimum effective daily amount of folic acid for women and the hormone-free daily units contain at least a multiple of this amount up to the maximum permissible amount of folic acid for women.

13 Claims, No Drawings

(56) References Cited

OTHER PUBLICATIONS

Non Final Office Action issued on Apr. 16, 2009 by Examiner for corresponding pending U.S. Appl. No. 11/348,545.
Non Final Office Action issued on Jul. 8, 2008 by Examiner for corresponding pending U.S. Appl. No. 11/009,938.
Non Final Office Action issued on Sep. 3, 2009 by Examiner for corresponding pending U.S. Appl. No. 11/009,938.
Final Office Action issued on Mar. 23, 2009 by Examiner for corresponding pending U.S. Appl. No. 11/009,938.
Non Final Office Action issued on Sep. 2, 2009 by Examiner for corresponding pending U.S. Appl. No. 11/009,362.
G. Schramm, Contraceptive Efficacy and Tolerability of Chlormadinone Acetate 2mg/Ethinylestradiol 0.03mg (Belara®), Clinical Drug Invest 2002:22 (4) pp. 221-231.

* cited by examiner

DOSAGE FORM FOR HORMONAL CONTRACEPTION

CROSS-REFERENCE TO RELATED APPLICATIONS

This application is a Continuation in Part Application of and claims priority from U.S. patent application Ser. No. 11/009,817, filed on Dec. 10, 2004, pending, and U.S. patent application Ser. No. 11/009,938 filed on Dec. 10, 2004, pending, and claims foreign priority to DE 10 2004 026 671.9, filed May 28. 2004.

BACKGROUND OF THE INVENTION

1. Field of the Invention

The present invention relates to a dosage form for hormonal contraception containing a given number of hormone-containing daily units and a given number of hormone-free daily units for uninterrupted daily oral administration to women, characterized in that the hormone-containing daily units contain folic acid in a daily amount of at most 200 μg and the hormone-free daily units in each case contain folic acid in a daily amount of >200 μg up to the maximum permissible amount of folic acid for women.

It is suspected that long-term taking of gestagen-based hormonal contraceptives may lead to a deficiency of folic acid. This deficiency may lead to cardiovascular diseases, for example.

It is also known that if pregnancy occurs a short time after stopping taking such hormonal contraceptives, there is a risk that the deficiency of folic acid may lead to neural tube defects in the embryo. Since the neural tube develops in the first weeks of pregnancy, it is particularly advantageous to ensure that folic acid is taken prior to conception.

If, therefore, a woman stops taking hormonal contraceptives because she wants to have a child and she falls pregnant in the first cycle after stopping the hormonal contraceptives, it is particularly important to ensure an appropriately high level of folic acid in the period directly after stopping taking the "Pill", as hormonal contraceptives are known.

There is therefore a need to add folic acid to hormonal contraceptives in such a way that the added folic acid is adapted to a woman's varying needs over the period during and after a tablet-taking cycle.

2. Brief Description of Related Developments

The combination of hormonal contraceptives and folic acid is already known from WO 99/53910. The amount of folic acid per daily dose of hormones merely matches the changes in a woman's folic acid requirements as she ages, and does not take account of the changes in folic acid requirements over a contraceptive-taking cycle.

SUMMARY OF THE INVENTION

It was therefore the object of the present invention to provide a dosage form for hormonal contraception which takes account of the changes in folic acid requirements during a hormone-taking cycle and subsequent hormone-free daily units.

This object was achieved by providing the dosage form according to the invention for hormonal contraception containing a given number of hormone-containing daily units and a given number of hormone-free daily units for uninterrupted daily oral administration to women, characterized in that the hormone-containing daily units contain folic acid in a daily amount of at most 200 μg and the hormone-free daily units in each case contain folic acid in a daily amount of >200 μg up to the maximum permissible amount for women of folic acid.

Women of child-bearing age have a daily folic acid requirement which may be adequately met by a healthy diet. Long term taking of hormonal contraceptives containing gestagens may lead to an additional folic acid requirement, which may likewise be met by a healthy diet. However, it is advisable to provide women with a daily dose of the minimum effective daily amount of folic acid.

Accordingly, hormone-containing daily units of the dosage form according to the invention may each comprise a daily amount of folic acid corresponding to this minimum effective daily amount of folic acid. Preferably, the hormone-containing daily units of the dosage form according to the invention contain 0 to 200 μg of folic acid, particularly preferably 5 to 200 μg of folic acid.

The hormone-containing daily units of the dosage form according to the invention may also not contain any additional folic acid, however.

To ensure that a woman consumes the necessary amount of folic acid or that her increased folic acid requirement at least at the beginning of pregnancy is met as quickly as possible if she decides to try for a baby, so avoiding possible damage to the embryo due to a folic acid deficiency, the hormone-free daily units of the folic acid dosage form according to the invention contain folic in an amount of more that 200 μg up to the maximum permissible daily amount of folic acid for women, preferably up to 5 mg of folic acid per daily unit, particularly preferably of more than 200 μg to 5 mg folic acid, very particularly preferably up to the maximum permissible daily amount of folic add for women of reproductive age.

By adding folic acid to the hormone-free daily units of the dosage form according to the invention in amounts of up to the maximum permissible amount, it is possible to increase the folic acid concentration in a woman's body while she is taking the hormone-free daily units to the extent that the her body's increased folic acid requirement is met as quickly as possible if she stops taking a hormone-containing contraceptive and then falls pregnant.

The hormone-containing daily units of the dosage form according to the invention preferably each contain the same amount of folic acid. This also applies to the hormone-free daily units, which likewise each contain the same amount of folic acid, this being greater than the amount contained in the hormone-containing daily units however.

The folic acid may also be present in the dosage form according to the invention as a pharmaceutically safe salt, preferably as sodium, potassium or magnesium salt, or as a corresponding derivative.

Suitable derivatives of folic acid are mono- or diesters, wherein the diesters may be differently or identically esterified. Suitable ester groups are preferably $C_1$-$C_8$ low alkyl groups, such as methyl, ethyl, propyl or butyl, branched $C_1$-$C_8$ low alkyl groups, such as isopropyl, isobutyl or sec.-butyl, cycloalkyl groups, such as cyclopentyl or cyclohexyl, aryl groups, such as phenyl or substituted phenyl with 1-2 substituents, such as low alkyl or haloalkoxyl groups, or arylalkyl groups with $C_1$-$C_8$ alkyl and aryl groups, such as phenyl or substituted phenyl.

In addition, the hormone-free daily units and optionally the hormone-containing daily units may contain further vitamins or minerals in addition to the folic acid.

The number of daily units of a dosage form according to the invention may correspond to a natural, monthly menstrual cycle. In this case, the dosage form according to the invention contains 21 to 25 hormone-containing daily units and 7 to 3 hormone-free daily units.

However, it is also possible for the total number of hormone-containing daily units to correspond to more than a woman's natural monthly cycle, such that a dosage form according to the invention may contain hormone-containing daily units to be taken without interruption for up to 2 years, preferably up to 1 year, and 7 to 3 hormone-free daily units. However, it is also possible for the dosage form according to the invention to comprise 42 to 52 or 77 to 193 hormone-containing daily units alongside 7 to 3 hormone-free daily units.

The hormone-containing daily units of the dosage form according to the invention may each contain at least one contraceptively acting hormone component, preferably a combination of hormone components such as an oestrogen and a gestagen.

Oestrogens which are suitable for the hormone-containing daily units of the dosage form according to the invention are preferably selected from the group comprising oestradiol, oestradiol valerate, ethinyloestradiol and mestranol. Ethinyioestradiol is particularly preferred as the oestrogen for the dosage form according to the invention.

Gestagens which are suitable for the hormone-containing daily units of the dosage form according to the invention are preferably selected from the group comprising norethisterone, norethisterone acetate, norethisterone enantate, norgestimate, norgestrel, levonorgestrel, gestodene, hydroxyprogesterone caproate, medroxyprogesterone acetate, megestrol acetate, chlormadinone acetate, lynestrenol, cyproterone acetate, drospirenone, dienogest, desogestrel, progesterone, dydrogesterone, medrogestone, ethynodiol, promegestone, nomegestrol acetate and trimegestone.

The hormones are preferably used in the amounts stated below.

Oestrogens:

| | |
|---|---|
| Oestradiol, oestradiol valerate | 0.5 to 4 mg |
| Ethinyloestradiol | 5 to 50 µg |
| Mestranol | 8 to 70 µg |

Gestagens:

| | |
|---|---|
| Norethisterone, norethisterone acetate | 0.5 to 1.0 mg |
| Norgestimate | 0.1 to 0.25 mg |
| Norgestrel | 0.3 to 1.0 mg |
| Levonorgestrel | 0.05 to 0.15 mg |
| Gestodene | 0.05 to 0.12 mg |
| Hydroxyprogesterone caproate | 10 to 800 mg |
| Medroxyprogesterone acetate | 2.5 to 40 mg |
| Megestrol acetate | 1.0 to 10 mg |
| Chlormadinone acetate | 0.5 to 10 mg |
| Lynestrenol | 0.4 to 3 mg |
| Cyproterone acetate | 0.5 to 10 mg |
| Drospirenone | 1.0 to 10 mg |
| Dienogest | 1.0 to 10 mg |
| Desogestrel | 0.06 to 0.30 mg |
| Progesterone | 100 to 1000 mg |
| Dydrogesterone | 5 to 50 mg |
| Medrogestone | 2 to 30 mg |
| Ethynodiol, ethynodiol diacetate | 0.4 to 3 mg |
| Promegestone | 0.5 to 10 mg |
| Nomegestrol acetate | 0.5 to 10 mg |
| Trimegestone | 1 to 10 mg |
| Etonogestrel | 0.1 to 1 mg |
| Norelgestromin | 0.1 to 2 mg |
| Norethynodrel | 0.3 to 3 mg |
| Tibolone | 1 to 10 mg |

The dosage forms according to the invention, especially the hormone-containing daily units, preferably comprise the following hormone combinations:
1. 0.015 mg ethinyloestradiol+0.06 mg gestodene
2. 0.02 mg ethinyloestradiol+0.15 mg desogestrel
3. 0.02 mg ethinyloestradiol+0.5 mg norethisterone
4. 0.02 mg ethinyloestradiol+1 mg chlormadinone acetate or 2 mg or 3 mg chlormadinone acetate
5. 0.02 mg ethinyloestradiol+1 mg norethisterone
6. 0.03 mg ethinyloestradiol+1 mg norethisterone
7. 0.02 mg ethinyloestradiol+4 mg chlormadinone acetate
8. 0.02 mg ethinyloestradiol+5 mg chlormadinone acetate
9. 0.02 mg ethinyloestradiol+0.1 mg levonorgestrel
10. 0.02 mg ethinyloestradiol+0.15 mg desogestrel
11. 0.02 mg ethinyloestradiol+0.1 mg levonorgestrel
12. 0.03 mg ethinyloestradiol+3 mg drospirenone
13. 0.02 mg ethinyloestradiol+3 mg drospirenone
14. 0.03 mg ethinyloestradiol+2 mg chlormadinone acetate
15. 0.035 mg ethinyioestradiol+0.25 mg norgestimate
16. 0.03 mg ethinyloestradiol+0.5 mg norethisterone
17. 0.03 mg ethinyloestradiol+0.15 mg desogestrel
18. 0.03 mg ethinyloestradiol+0.075 mg gestodene
19. 0.03 mg ethinyloestradiol+0.15 mg levonorgestrel
20. 0.03 mg ethinyloestradiol+0.15 mg desogestrel
21. 0.03 mg ethinyloestradiol+0.15 mg levonorgestrel
22. 0.03 mg ethinyloestradiol+0.125 mg levonorgestrel
23. 0.0375 mg ethinyloestradiol+0.75 mg lynestrenol
24. 0.03 mg ethinyloestradiol+1 mg norethisterone
25. 0.03 mg ethinyloestradiol+0.5 mg norethisterone
26. 0.03 mg ethinyioestradiol+0.15 mg levonorgestrel
27. 0.04 mg ethlnyloestradiol+2 mg lynestrenol
28. 1st phase=7 days
    0.050 mg desogestrel +0.035 ethinyloestradiol
    2nd phase=7 days
    0.100 mg desogestrel +0.030 ethinyloestradiol
    3rd phase=7 days
    0.150 mg desogestrel +0.030 ethinyloestradiol
29. 1st phase=6 days
    0.03 mg EE +0.05 mg levonorgestrel
    2nd phase=5 days
    0.04 mg EE +0.075 mg levonorgestrel
    3rd phase=10 days
    0.03 mg EE +0.125 mg levonorgestrel
30. 1st phase=7 days
    0.035 mg EE +0.180 mg norgestimate
    2nd phase=7 days
    0.035 mg EE +0.215 mg norgestimate
    3rd phase=7 days
    0.035 mg EE +0.250 mg norgestimate
31. 1st phase=6 days
    0.03 mg EE +0.05 mg levonorgestrel
    2nd phase=5 days
    0.04 mg EE +0.075 mg levonorgestrel
    3rd phase=10 days
    0.03 mg EE +0.125 mg levonorgestrel
32. 1st phase=7 days
    0.035 mg EE +0.5 mg norethisterone
    2nd phase=9 days
    0.035 mg EE +1 mg norethisterone
    3rd phase=5 days
    0.035 mg EE +0.5 mg norethisterone
33. 1st phase=6 days
    0.03 mg EE +0.05 mg levonorgestrel
    2nd phase=5 days
    0.04 mg EE +0.075 mg levonorgestrel
    3rd phase=10 days
    0.03 mg EE +0.125 mg levonorgestrel 34. 1st phase=7 days
   0.035 mg EE+0.5 mg norethisterone
   2nd phase=7 days
   0.035 mg EE+0.75 mg norethisterone
   3rd phase=7 days
   0.035 mg EE+1 mg norethisterone
35. 1st phase=6 days
   0.03 mg EE+0.05 mg levonorgestrel
   2nd chase=5 days
   0.04 mg EE+0.075 mg levonorgestrel
   3rd phase=10 days
   0.03 mg EE+0.125 mg levonorgestrel
36. 1st phase=6 days
   0.03 mg EE+0.05 mg levonorgestrel
   2nd phase=6 days
   0.04 mg EE+0.075 mg levonorgestrel
   3rd phase=9 days
   0.03 mg EE+0.125 mg levonorgestrel
37. 1st phase=6 days
   0.03 mg EE+0.05 mg levonorgestrel
   2nd phase=5 days
   0.05 mg EE+0.05 mg levonorgestrel
   3rd phase=10 days
   0.04 mg EE+0.125 mg levonorgestrel
38. 1st phase=6 days
   0.03 mg EE+0.05 mg levonorgestrel
   2nd phase=5 days
   0.04 mg EE+0.075 mg levonorgestrel
   3rd phase=10 days
   0.03 mg EE+0.125 mg levonorgestrel
39. 0.035 mg ethlnyloestradiol+2 mg cyproterone acetate
40. 0.05 mg mestranol+2 mg chlormadinone acetate
41. 1st phase=11 days
   0.05 mg ethinyloestradiol+1 mg chlormadinone acetate
   2nd phase=11 days
   0.05 mg ethinyloestradiol+2 mg chlormadinone acetate
42. 0.08 mg mestranol+2 mg chlormadinone acetate
43. 0.03 mg ethlnyloestradiol+2 mg dienogest
44. 0.05 mg ethinyloestradiol+0.5 mg norgestrel
45. 0.05 mg ethinyloestradiol+0.125 mg levonorgestrel
46. 0.05 mg ethinyloestradiol+0.25 mg levonorgestrel
47. 0.05 mg ethinyloestradiol+0.125 mg levonorgestrel
48. 0.05 mg ethinyloestradiol+1 mg norethisterone acetate
49. 0.05 mg ethinyloestradiol+0.25 mg levonorgestrel
50. 1st phase=7 days
   0.04 mg ethinyloestradiol+0.025 mg desogestrel
   2nd phase=15 days
   0.03 mg ethinyloestradiol+0.125 mg desogestrel
51. 1st phase=11 days
   0.05 mg ethinyloestradiol+0.05 mg levonorgestrel
   2nd phase=10 days
   0.05 mg ethinyloestradiol+0.125 mg levonorgestrel
52. 1st phase=11 days
   0.05 mg ethlnyloestradiol+0.05 mg levonorgestrel
   2nd phase=10 days
   0.05 mg ethinyloestradiol+0.125 mg levonorgestrel
53. 1st phase=7 days
   0.05 mg ethinyloestradiol+
   2nd phase=15 days
   0.05 mg ethinyloestradiol+2.5 mg lynestrenol
54. 1st phase=7 days
   0.05 mg ethinyloestradiol+
   2nd phase=15 days
   0.05 mg ethlnyloestradiol+0.125 mg desogestrel
55. 1st phase=6 days
   0.05 mg ethinyloestradiol+
   2nd phase=15 days
   0.05 mg ethinyloestradiol+1 mg norethisterone acetate Where the dosage form according to the invention provides a multiphasic hormone combination, it is recommended that the hormone-containing daily units be taken without interruption only for a period of 21 to 25 days, followed by 7 to 3 days of taking hormone-free daily units.

The dosage form according to the invention preferably comprises at least 21, preferably 21 to 25, hormone-containing daily units which preferably include 5 to 30 μg of ethinyloestradiol and 0.5 to 5 mg of chlormadinone acetate, and 3 to 7 hormone-free daily units. However, the dosage form according to the invention may also comprise hormone-containing daily units for several years, preferably of 42 to 365 units, which contain the stated hormone combination in the stated ranges, wherein the corresponding uninterrupted tablet-taking periods are followed by 7 to 3 hormone-free daily units with an elevated amount of folic acid stated according to the invention.

As already stated, the hormone-containing daily units of the dosage form according to the invention may take the form of a monophasic (one-phase) or multiphasic contraceptive. In the case of a multiphasic contraceptive, a two-phase or a three-phase pill may be present, which is not usually suitable, however, to be taken for a period longer than a woman's natural cycle.

The dosage form according to the invention may also be a constituent of a kit, wherein the kit according to the invention may comprise a plurality of the dosage forms according to the invention, especially if one dosage form comprises only one monthly cycle. The kit may optionally include a calendar or a diary.

EXAMPLES

Example 1 a) Composition

|  | Per tablet |
| --- | --- |
| Ethinyloestradiol | 0.020 mg |
| Chlormadinone acetate | 2.000 mg |
| Povidone K30 | 3.000 mg |
| Lactose | 31.980 mg |
| Maize starch | 12.000 mg |
| Magnesium stearate | 0.500 mg |
| Highly disperse silicon dioxide | 0.500 mg |

Ethinyloestradiol (EE) and povidone K30 (polyvinylpyrrolidone) were dissolved in 600 ml of ethanol. Chlormadinone acetate (particle size 90% <50 μm), lactose and maize starch were mixed in a mixer/pelletiser (Diosna P25) for 5 mins. and then moistened thoroughly and mixed with the ethanolic EE/PVP solution. The moist composition was forced through a 3 mm screen and dried in a vacuum drying cabinet. The dried granular product was disagglomerated through a 0.6 mm screen, mixed with magnesium stearate and highly disperse silicon dioxide and pressed on a tablet press with 5 mm punches into tablets with a weight of 50 mg.

b) As indicated under a), hormone-free, folic acid-containing tablets with a weight of 50 mg were produced, wherein the sodium salt of the folic acid was dissolved in 600 ml of aqueous ethanol.

|  | Per tablet |
| --- | --- |
| Sodium folate | 3.000 mg |
| Povidone K30 | 3.000 mg |
| Lactose | 31.000 mg |
| Maize starch | 12.000 mg |
| Magnesium stearate | 0.500 mg |
| Highly disperse silicon dioxide | 0.500 mg |

The tablets were coated with a methylhydroxypropylcellulose-based coating (e.g. Opadry YS-1-2184 made by Colorcon), coating composition 2 mg per tablet, and packaged into a dosage form comprising 120 hormone-containing daily units without folic acid and 7 hormone-free daily units with folic acid.

What is claimed is:

1. A hormonal contraceptive dosage form for uninterrupted daily oral administration to women, said dosage form comprising hormone-containing daily units and hormone-free daily units, wherein each of the hormone-containing daily units comprises folic acid in a daily amount of from between about 5 to 200 μg and a combination of an oestrogen and a gestagen, and each of the hormone-free daily units comprises folic acid in a daily amount of greater than 200 μg up to the maximum permissible amount of folic acid for women.

2. A dosage form according to claim 1, wherein the hormone-free daily units each comprises more than 200 μg and up to 5 mg of folic acid.

3. A dosage form according to claim 1, wherein the hormone-containing daily units each comprises the same amount of folic acid and the hormone-free daily units likewise each comprises the same amount of folic acid.

4. A dosage form according to claim 1, wherein the dosage form comprises at least 21 hormone-containing daily units and 7 to 3 hormone-free daily units.

5. A dosage form according to claim 4, wherein the number of hormone-containing daily units is sufficient for administration for a maximum of 2 years, and the number of hormone-free daily units is sufficient for administration for to 7 to 3 days.

6. A dosage form according to claim 4, comprising up to 730 hormone-containing daily units and 7 to 3 hormone-free daily units.

7. A dosage form according to claim 4, which comprises 21 to 25 hormone-containing daily units and 7 to 3 hormone-free daily units.

8. A dosage form according to claim 4, which comprises 42 to 52 hormone-containing daily units and 7 to 3 hormone-free daily units.

9. A dosage form according to claim 4, which comprises 77 to 193 hormone-containing daily units and 7 to 3 hormone-free daily units.

10. A dosage form according to claim 1, wherein the number of hormone-containing daily units corresponds to a monophasic contraceptive.

11. A kit comprising at least one dosage form for hormonal contraception according to claim 1.

12. A kit according to claim 11, wherein the kit comprises a plurality of dosage forms.

13. A dosage form according to claim 6, wherein the dosage form comprises up to 365 hormone-containing daily units and 7 to 3 hormone-free daily units.

* * * * *